(12) United States Patent
Chaplin

(10) Patent No.: US 7,358,334 B1
(45) Date of Patent: Apr. 15, 2008

(54) B CELL-TARGETED TOXINS FOR HUMORAL IMMUNE RESPONSE REDUCTION AND METHODS OF USE THEREOF

(76) Inventor: Jay W Chaplin, 1276 Warner Ave., Los Angeles, CA (US) 90024

( * ) Notice: Subject to any disclaimer, the term of this patent is extended or adjusted under 35 U.S.C. 154(b) by 415 days.

(21) Appl. No.: 10/985,487

(22) Filed: Nov. 10, 2004

Related U.S. Application Data

(60) Provisional application No. 60/520,520, filed on Nov. 14, 2003, provisional application No. 60/588,515, filed on Jul. 16, 2004.

(51) Int. Cl.
*C07K 14/00* (2006.01)
*C12N 9/00* (2006.01)
(52) U.S. Cl. .................................. 530/350; 435/183
(58) Field of Classification Search ................ None
See application file for complete search history.

(56) References Cited

U.S. PATENT DOCUMENTS

| | | | |
|---|---|---|---|
| 4,664,911 A | 5/1987 | Uhr et al. | |
| 5,677,274 A | 10/1997 | Leppla et al. | |
| 5,686,072 A | * 11/1997 | Uhr et al. ................ | 424/183.1 |
| 5,696,238 A | 12/1997 | Haigwood et al. | |
| 5,767,072 A | 6/1998 | Vitetta et al. | |
| 5,830,478 A | 11/1998 | Raso et al. | |
| 6,103,238 A | 8/2000 | Essex et al. | |
| 6,140,059 A | 10/2000 | Schawaller | |
| 6,156,952 A | 12/2000 | Bryant et al. | |
| 6,193,982 B1 | 2/2001 | Boyd | |
| 6,248,574 B1 | 6/2001 | Shaffermann | |

OTHER PUBLICATIONS

Janeway et al. Immunobiology: The immune system in health and disease, 2nd edition, Garland Publishing, 1996.*
Panikar, Botulinum toxins: Pharmacology and its current therapeutic evidence for use, Neurology India, 2003, 51(4):455-460.*
Cook et al., Tetanus: a review of the literature, British Journal of Anaesthesia, 2001, 87(3):477-87.*
Blanke et al., Fused polycationic peptide mediates delivery of diphtheria toxin A chain to the cytosol in the presence of anthrax protective antigenProc. Natl. Acad. Sci. USA, 1996, 93:8437-8442.*
Milne et al., Protective antigen-binding domain of anthrax lethal factor mediates translocation of a heterologous protein fused to its amino- or carboxy-terminus, Molecular Microbiology, 1995, 15(4):661-6. (Abstract only).*
Ada, G. L., and Byrt, P. 1969. Specific inactivation of antigen-reactive cells withv125I-labeled antigen. Nature. 222: 1291-1295.
Albert, J., Abrahamsson, B., Nagy, K., et al., Rapid development of isolate-specific neutralizing antibodies after primary HIV- 1 infection and consequent emergence of virus variants which resist neutralization by autologous sera. AIDS 4:107-112, 1990.

Banda, N., Bernier, J., Kurahara, D., et al. 1992. Crosslinking CD4 by human immunodeficiency virus gp120 primes T cells for activation-induced apoptosis. J. Exp. Med. 176:1099-1106.
Borrow, P., Lewicki, H., Hahn, B., Shaw, G., and Oldstone, M., Virus-specific CD8+ cytotoxic T-lymphocyte activity associated with the control of viremia in primary human immunodeficiency virus type 1 infection. J. Virol. 68:6103-6110, 1994.
Carotenuto, et al., "Neutralizing antibodies are positively associated with CD4+ T-cell counts and T-cell function in long-term AIDS-free infection", AIDS, (1998), vol. 12(13), pp. 1591-1600.
Chaplin, HIV pathogenesis: gp120-antibody complexes bind CD4 and kill T4 cells; immunotoxin therapy should prevent the progression of HIV to AIDS. Med. Hypoth. 52:133-146, 1999.
Choe, S., Bennett, M., Fuji, G., et al. 1992. The crystal structure of Diphtheria toxin. Nature. 357:216-357Clerici, M., and Shearer, G., A TH1 to TH2 switch is a critical step in the etiology of HIV infection. Immunol. Today. 14:107- 110, 1993.
Clerici, M., Sarin, A., Coffman, R., et al., Type 1/type 2 cytokine modulation of T-cell programmed cell death as a model for human immunodeficiency virus pathogenesis. Proc. Natl. Acad. Sci. 91:11811-11815, 1994.
Desbarats, J., Freed, J., Campbell, P., and Newell, M. 1996. Fas (CD95) expression and death-mediating function are induced by CD4 crosslinking on CD4+ T cells. Proc. Natl. Acad. Sci. 93:11014-11018.
D'Souza, M., and Mathieson, B., Early phases of HIV type 1 infection. AIDS Res. and Hum. Retro. 12:1-9, 1996.
Earl, P., Koenig, S., and Moss, B., Biological and immunological properties of human immunodeficiency virus type 1 envelope glycoprotein: analysis of proteins with truncations and deletions expressed by recombinant vaccina viruses. J. Virol. 65:31-41, 1991.
Fan, J., Bass, H., and Fahey, J., Elevated IFN- and decreased IL-2 gene expression are associated with HIV infection. J. Immunol. 151:5031-5040, 1993.
Finco, O., Nuti, S., De Magistris, M. T., et al. 1997. Induction of CD4+ T cell depletion in mice doubly transgenic for HIV gp120 and human CD4. Eur. J. Immunology. 27: 1319-1324.
Finkel, T., Tudor-Williams, G., Banda, N., et al. 1995. Apoptosis occurs predominantly in bystander cells and not in productively infected cells of HIV- and SIV-infected lymph nodes. Nat. Med. 1:129-134.
Graziosi, C., Grant, K., Vaccarezza, M., et al. 1996. Kinetics of cytokine expression during primary human immunodeficiency virus type 1 infection. Proc. Natl. Acad. Sci. 93:4386-4391, 1996.
Goodglick et al., Mapping the IG Superantigen-Binding Site of HIV-1 gp120, J. Immunol. 155:5151-5159, 1995.

(Continued)

*Primary Examiner*—Bruce R. Campell
*Assistant Examiner*—Kinsey White
(74) *Attorney, Agent, or Firm*—McDonnell Boehnen Hulbert & Berghoff LLP

(57) ABSTRACT

Disclosed herein are compositions and methods for selectively inhibiting and/or killing a target sub-population of B cells.

20 Claims, 4 Drawing Sheets

OTHER PUBLICATIONS

Groux, H., Bigler, M., de Vries, J., and Roncarolo, M., Interleukin-10 induces a long-term antigen-specific anergic state in human CD4+ T cells. J. Exp. Med. 184:19-29, 1996.

Kang, Y., Melo, E. F. M., Scott, D. 1998. An ongoing immune response to HIV envelope gp120 in human CD4-transgenic mice contributes to T cell decline upon intravenous administration of gp120. Eur. J. Immunology. 28:2253-2264.

Karray and Zouali, Identification of the B cell superantigen-binding site of HIV-1 gp120, Proc. Natl. Acad. Sci. U.S.A. 94:1356-60, 1997.

Klein, et al., "Demonstration of the Th1 to Th2 cytokine shift during the course of HIV-1 infection using cytoplasmic cytokine detection on single cell level by flow cytometry", AIDS, (1997), pp. 1111-1118.

Koup, R., Safrit, J., Cao, Y., et al., Temporal association of cellular immune responses with the initial control of viremia in primary human immunodeficiency virus type 1 syndrome. J. Virol. 68:4650-4655, 1994.

McDougal, J., Kennedy, M., Sligh, J., Cort, S., Mawle, A., and Nicholson, J., Binding of HTLV-III/LAV to T4+ cells by a complex of the 110K viral protein and the T4 molecule. Science. 231:382-385, 1986.

Mittler, R., and Hoffman, M. 1989. Synergism between HIV gp120 and gp120-specific antibody in blocking human T cell activation. Science. 245:1380-1382.

Meroni, L., Trabattoni, D., Balotta, C., et al. 1996. Evidence for type 2 cytokine production and lymphocyte activation in the early phases of HIV-1 infection. AIDS. 10:23-30, 1996.

Oyaizu, N., Chirmule, N., Kalyanaraman, V., Hall, W., Good, R., and Pahwa, S. 1990. Human immunodeficiency virus type 1 envelope glycoprotein gp120 produces immune defects in CD4+ T lymphocytes by inhibiting interleukin 2 mRNA. Proc. Natl. Acad. Sci. USA 87:2379-2383.

Saavedra-Lozano, et al., (An Anti-CD45RO) Immunotoxin Kills Latently Infected Human Immunodeficiency Virus (HIV) CD4 T Cells in the Blood of HIV-Positive Persons, The Journal of Infectious Diseases, (2002), pp. 306-314.

Skowron, G., Cole, B., Zheng, D., Acetta, G., and Yen-Lieberman, B. 1997. gp120-directed antibody-dependent cellular cytotoxicity as a major determinant of the rate of decline in CD4 percentage in HIV-1 disease. AIDS. 11:1807-1814.

Tamalet, C., Lafeuillade, A., Tourres, C., Yahi, N., Vignoli, C., and De Mico, P., Inefficacy of neutralizing antibodies against autologous lymph-node HIV-1 isolates in patients with early-stage HIV. AIDS. 8:388-389, 1994.

Wang, Z., Orlikowsky, T., Dudhane, A., et al. 1994. Deletion of T lymphocytes in human CD4 transgenic mice induced by HIV-gp120 and gp120-specific antibodies from AIDS patients. Eur. J. Immunol. 24:1553-1557.

Weinhold, K., Lyerly, H., Stanley, S., Austin, A., Matthews, T., and Bolognesi, D. 1989. HIV-1 gp120-mediated immune suppression and lymphocyte destruction in the absence of viral infection. J. Immunol. 142:3091-3097.

Williams, D., Snider, C., Strom, T., and Murphy, J. 1990. Structure/function analysis of interleukin-2-toxin (DAB486-IL-2). J. Biol. Chem. 265:11885-11889.

Wyatt et al., The antigenic structure of HIV gp120 envelope glycoprotein, Nature 393:705-711, 1998.

Zanussi, S., Simonelli, C., D'Andrea, M., et al., CD8+ lymphocyte phenotype and cytokine production in long-term non-progressor and in progressor patients with HIV-1 infection. Clin. Exp. Immunol. 105:220-224, 1996.

Yang, O., Kalams, S., Rosenzweig, M., et al., Efficient lysis of human immunodeficiency virus type 1-infected cells by cytotoxic T lymphocytes. J. Virol. 70:5799-5806, 1996.

Arora, N., Klimpel, K., Singh, Y., and Leppla, S. Journal of Biological Chemistry, vol. 267, No. 22, pp. 15542-15548, 1992.

Ballard, J., Collier, R.J., and Starnbach, M. PNAS, vol. 93, pp. 12531-12534, 1996.

Ballard, J., Doling, A., et al. Infection and Immunity, vol. 66, No. 2, pp. 615-619, 1998.

Ballard, J., Collier, R.J., and Starnbach, M. Infection and Immunity, vol. 66., No. 10, pp. 4696-4699, 1998.

Lu, Y., Friedman, R., et al., PNAS, vol. 97, No. 14, pp. 8027-8032, 2000.

Sandvig, K., and van Deurs, B. Annu, Rev. Cell Dev. Biol. vol. 18, pp. 1-24, 2002.

* cited by examiner

FIGURE 1 comprising a modified HIV clade C gp120 sequence.

```
mkvke  trrny  qhlwr  wgiml  lgilm  icsat  eklwv  tvyyg
vpvwk  eattt  lfcas  dakay  dtevh  nvwat  hacvp  tdpnp
qevvl  gnvte  nfnmw  knnmv  eqmqe  diisl  wdqsl  kpcvk
ltvtl  nctdl  gkatn  ttssn  wekme  kgeik  ncsfn  ittsi
rdkvq  keyal  fykld  ivpid  nnsnt  tnnts  yrlis  cntsv
itqac  pkvsf  epipi  hyctp  agfai  lkcnd  kkfng  kgpck
nvstv  qcthg  irpvv  stqll  lngsl  aeeev  virse  nftnn
aktii  vqlke  svein  ctrpn  nntrk  sihig  pgAaf  yttge
iigdi  rqahc  nisra  kwnnt  lkqiv  kklre  qfgnk  ivfnq
ssggK  pRivt  hsfnc  ggeff  ycntt  qlfns  tTTRs  tnnte
gsnnt  dtitt  lpcrA  DAiin  rwqev  gkamy  appir  gqirc
ssnit  glllt  rdggt  ntndt  eifrp  gggdm  rdnwr  selyk
ykvvk  ieplg  vaptk  akrrv  vqrek  r
```

FIGURE 2 comprising a modified Human IL-4 sequence.

```
hkcdi  tlqei  iktln  slten  ktlct  eltvt  difaa  skntt  eketf  craat
vlrqf  yshhe  kdtrc  lgata  qqfhr  hkqli  rflkr  ldrnl  wglag  lnscp
vkean  qstle  nfler  lktim  rekDs  kcss
```

FIGURE 3 comprising a modified Anthrax Protective Antigen sequence.

<u>evkqe nrlln esess sqgll</u> gyyfs dlnfq apmvv tsstt gdlsi pssel
enips enqyf qsaiw sgfik vkksd eytfa tsadn hvtmw vddqe vinka
snsnk irlek grlyq ikiqy qrenp tekgl dfkly wtdsq nkkev issdn
lqlpe lkqks snsrk krsts agptv pdrdn dgipd sleve gytvd vknkr
tflsp wisni hekkg ltkyk sspek wstas dpysd fekvt gridk nvspe
arhpl vaayp ivhvd menii lskne dqstq ntdse trtis kntst srtht
sevhg naevh asffd iggsv sagfs nsnss tvaid hslsl agert waetm
glnta dtarl nanir yvntg tapiy nvlpt tslvl gknqt latik akenq
lsqil apnny ypskn lapia lnaqd dfsst pitmn ynqfl elekt kqlrl
dtdqv ygnia tynfe ngrvr vdtgs nwsev lpqiq ettar iifng kdlnl
verri aavnp sdple ttkpd mtlke alkia fgfne pngnl qyqgk ditef
dfnfd qqtsq niknq laeln atniy tvldk iklna kmnil irdkr fhydr
nniav <u>gades vvkea hrevi nsste gllln idkdi rkils gyive iedte
glkev indry dmlni sslrq dgktf idfkk yndkl plyis npnyk vnvya
vtken tiinp sengd tstng ikkil ifskk gyeig</u>

FIGURE 4 comprising a modified Diphtheria Toxin A chain sequence.

gaddv vdssk sfvme nfssy hgtkp gyvds iqkgi qkpks gtqgn ydddw
kgfys tdnky daagy svdne nplsg kaggv vkvty pgltk vlalk vdnae
tikke lglsl teplm eqvgt eefik rfgdg asrvv lslpf aegss sveyi
nnweq akals velei nfetr gkrgq damye ymaqa cagnr vrr

FIGURE 5 comprising an acid-dependant polycationic octahistidine tract, followed by a linker segment, followed by sequence from Figure 5 (truncated DTA), followed by a proteolytically cleavable linker, followed by a modified consensus C clade HIV gp120 sequence from Figure 1.

```
hhhhh hhhss gssgg addvv dssks fvmen fssyh gtkpg yvdsi qkgiq
kpksg tqgny dddwk gfyst dnkyd aagys vdnen plsgk aggvv kvtyp
gltkv lalkv dnaet ikkel glslt eplme qvgte efikr fgdga srvvl
slpfa egsss veyin nweqa kalsv elein fetrg krgqd amyey maqas
agnrv rrssg rvrrs sgssg mrvrg tlrny qqwei wgilg fwmlm icnvg
gnlwv tvyyg vpvwk eaktt lfcas dakay ekevh nvwat hacvp tdpnp
qeivl envte nfnmw kndmv nqmhe dvisl wdqsl kpcvk ltplc vtlec
rnvts ngtty tesve eiknc sfntt teird rkqkv yalfy rldiv plnen
nsnss nssey yrlin cntsa itqac pkvtf dpipi hycap agyai lkcnd
ktfng tgpch nvstv qcthg ikpvv stqll lngsl aegei iirse nltnn
vktii vhlnq sveiv ctrpn nntrk sirig pgqtf yatge iigdi rqahc
nised kwnet lqrvg kklae hfpnk tikfa sssgg kprit thsfn crgef
fycnt sglfn gtttr tdtkn ssnsn titip crada iinmw qevgr amyap
piegn itcks nitgl llvrd ggtee tnkte tfrpg ggdmr dnwrs elyky
kvvei kplgv aptea krrvv erekr
```

FIGURE 6 comprising a sequence from Figure 4 (truncated Anthrax PA), followed by a linker, followed by a sequence from Figure 3 (hIL-4 antagonist).

```
llgyy fsdln fqapm vvtss ttgdl sipse lenip senqy fqsai wsgfi
kvkks deytf atsad nhvtm wvddq evink asnsn kirle kgrly qikiq
yqren ptekg ldfkl ywtds qnkke vissd nlqlp elkqk ssnsr vrrst
sagpt vpdrd ndgip dslev egytv dvknk rtfls pwisn ihekk gltky
ksspe kwsta sdpys dfekv tgrid knvsp earhp lvaay pivhv dmeni
ilskn edqst qntds etrti sknts tsrth tsevh gnaev hasff digsv
sagfs nsnss tvaid hslsl agert waetm glnta dtarl nanir yvntg
tapiy nvlpt tslvl gknqt latik akenq lsqil apnny ypskn lapia
lnaqd dfsst pitmn ynqfl elekt kqlrl dtdqv ygnia tynfe ngrvr
vdtgs nwsev lpqiq ettar iifng kdlnl verri aavnp sdple ttkpd
mtlke alkia fgfne pngnl qyqgk ditef dfnfd qqtsq niknq laeln
atniy tvldi klnak mnili rdkrs sgssg hkcdi tlqei iktln slten
ktlct eltvt difaa skntt eketf craat vlrqf yshhe kdtrc lgata
qqfhr hkqli rflkr ldrnl wglag lnscp vkean qstle nfler lktim
rekds kcss
```

B CELL-TARGETED TOXINS FOR HUMORAL IMMUNE RESPONSE REDUCTION AND METHODS OF USE THEREOF

CROSS-REFERENCE TO RELATED APPLICATIONS

The present Utility patent application claims priority to the following U.S. Provisional patent applications: application No. 60/520,520 entitled "Compositions and Methods of Use of Highly Selective B Cell Clonal Toxins for Humoral Immune Response" filed on Nov. 14, 2003; and application No. 60/588,515 entitled "B Cell Targeted-Toxins and Methods of Use Thereof" and filed on Jul. 16, 2004

REFERENCE TO SEQUENCE LISTING, A TABLE, OR A COMPUTER LISTING APPENDIX

This application refers to a "Sequence Listing" listed below, which is provided as an electronic document on three compact discs (CD). One CD is labeled "replacement copy 1" containing a 26,663 bytes ASCII text file named "CHAP01_sequence_listing.txt". The second CD is labeled "replacement copy 2" and contains the same 26,663 bytes ASCII text file named "CHAP01_sequence_listing.txt". The third CD is labeled "CRF" and contains the same 26,663 bytes ASCII text file named "CHAP01_sequence_listing.txt". Each disc referenced above is part of a duplicate set and is identical to the other disc of the set. All the identical copies of "CHAP01_sequence_listing.txt" were created on Aug. 17, 2005. No other file than "CHAP01_sequence_listing.txt" is contained on each CD. That is, the above referenced compact discs each only contains the ASCII text file "CHAP01_sequence_listing.txt" (26,663 bytes, created on Aug. 17, 2005), which information contained therein is hereby incorporated by reference in its entirety herein.

FIELD OF THE INVENTION

The present invention relates directly to the treatment of autoimmune and immune-complex diseases, including forms of acquired immunodeficiency. In particular, multicomponent B-cell toxins are described for use in reducing or eliminating deleterious antibody responses via highly specific immunosuppression, thereby treating a subject suffering from an antibody-based autoimmune disease or similar condition. More particularly, the invention relates to compositions and methods of use of novel multicomponent B cell clonal toxins incorporating independent targeting moieties attached to interdependant toxic moieties. There is a long felt need in the art for efficient and directed means of deleting a deleterious antibody response for the treatment of autoimmune and immunodefeicency diseases in mammals despite the presence of pre-existing antibody populations. The present invention satisfies this need by providing a novel and highly specific method for reversing existing autoimmunity.

BACKGROUND

B-cells participate in the removal of foreign antigens from the body by using a surface molecule to bind the antigen or by making specific antibodies that can search out and destroy specific foreign antigens. Each B-cell is specific for one antigen and will only produce antibodies against the same antigen that it bears the surface receptor for. However each B-cell can only make antibodies when it has bound its particular foreign antigen and received the appropriate approval signal from a T4 (helper T) cell. Once the T4 cell approval has been delivered to the B-cell the B-cell may continue producing antibodies as long as the foreign antigen is present.

In some cases the antibodies produced by the specific B-cells will inappropriately target host cells or antigens. For example, in certain autoimmune diseases, B-cells mistakenly make antibodies against tissues of the body (self antigens) instead of foreign antigens or make antibodies to foreign antigens that have enough similarity to self antigens to cause appropriately made antibodies to also react against tissues of the host's body. These auto-antibodies may interfere with the normal function of the tissues or initiate destruction of the tissues. For instance, people with myasthenia gravis experience muscle weakness because autoantibodies produced by host B-cells attack a part of the nerve that stimulates muscle movements. Similarly, in the skin disease pemphigus vulgaris, auto-antibodies are misdirected against proteins that form the junctions between skin cells. The accumulation of these antibodies in between the skin layers causes severe skin blistering and death.

Other diseases in which antibodies mediate unwanted effects such as cell death include AIDS. AIDS has become a major cause of death in large parts of the world, with at least 40 million HIV infected individuals worldwide as of 2000 (U.S. Pat. No. 6,156,952). Recent improvements in therapy, such as the use of retroviral protease inhibitors, have been effective to decrease the mortality rates from AIDS. However, such therapies require continued use of expensive pharmaceuticals for the life of the infected individual. It appears that long-term use of such compounds may result in the development of resistant strains of HIV, as observed with earlier anti-HIV treatments like azidothymidine (AZT). Further, the expense of such treatments and demanding dosage regimens has prevented their widespread application in developing countries with some of the highest rates of HIV infection. A need exists for effective new therapies that can reduce or prevent the development of AIDS, preferably with a limited number or frequency of treatments.

It is almost universally agreed that AIDS is causally related to HIV infection, although the process by which HIV results in the immune system dysfunction characteristic of AIDS is still poorly understood. AIDS is characterized by a progressive depletion of CD4 positive immune cells (CD4+) from the host's system, including depletion of T4 helper/inducer cells (U.S. Pat. No. 5,767,072).

Early in HIV infection the immune response is largely cell-mediated, a few weeks after primary infection a vigorous HIV-specific cytotoxic T (T8) cell response develops and HIV levels decrease to nearly undetectable levels (Borrow et al., 1994; D'Souza and Mathieson, 1996; Koup et al., 1994). The initial antibodies produced in response to HIV infection are usually highly strain-specific and rapidly lose efficacy as the original HIV strain mutates (Koup et al., 1994; Albert et al., 1990; Tamalet et al., 1994). The high mutation rate intrinsic to retroviruses allows the HIV variants remaining in the host to escape immune surveillance and proliferate. For this reason, antibody therapy directed against HIV itself has not proven effective to date in preventing disease progression.

Following infection, the level of interleukin 2 (IL-2) production by T4 cells declines over a period of several years (Fan et al., 1993; Clerici and Shearer, 1993). There is a corresponding increase in levels of L-4 and IL-10, resulting in B cell activation and antibody overproduction (Graziosi et al., 1996). The resulting shift from a T8 and natural killer response to a B cell response is typical of individuals who will progress to full-blown AIDS (Fan et al., 1993; Clerici et al., 1993; Clerici et al., 1994; Meroni et al., 1996). This imbalance in interleukin production results in a feedback loop that further inhibits L-2 production as a result of increased L-10 levels (Groux et al., 1996). Decreased IL-2 production in turn contributes to the loss of T cell function (Chaplin, 1999).

One of the major antigenic determinants for host immune response to HIV is the gp120 glycoprotein which is the only HIV protein significantly exposed to the host's blood and lymph (Chaplin, 1999, Med. Hypoth. 52:133-146; U.S. Pat. No. 6,248,574). The gp120 protein is produced in precursor form by the env gene of HIV, which encodes a 160 kD glycoprotein (gp160) (U.S. Pat. No. 6,103,238). The gp160 protein is expressed in infected host cells and then cleaved into the extracellular surface protein gp120 and a transmembrane protein gp41. The transmembrane gp41 protein provides an anchor to which gp120 is somewhat loosely bound on the surface of HIV and infected host cells (Earl et al., 1991, J. Viro. 65:31-41).

Generally, the gp120 sequence can be divided into five variable regions (V1-V5) with 25% or less conserved sequences and five constant regions (C1-C5) with 75% or more sequence conservation, with immunologic determinants present on both constant and variable regions (Karry and Zouali, 1997). Variable regions V1-V4 form exposed loops anchored by disulphide bonds, while constant regions are concentrated in the core of the protein (Wyatt et al., 1998, Nature 393:705-711). The gp120 core, comprised of an inner domain, outer domain and a "bridging" anti-parallel β-sheet, has been reported to exhibit CD4 binding (Wyatt et al., 1998, Nature 393:705-711). Amino and carboxyl terminal sequences of gp120 are involved in gp41 binding (Wyatt et al., 1998, Nature 393:705-711).

Infection of T4 cells and macrophages by HIV is mediated by binding of gp120 to the CD4 receptor protein on the cell surface. (McDougal et al., 1986, Science 231:382-385). HIV is internalized into the cell and replicates by producing new viral genomes and viral proteins, including gp41 and gp120. New virions are produced by budding off from the infected cell membrane (Chaplin, 1999, Med. Hypoth. 52:133-146). About half of the gp120 protein produced is shed into the circulation, where it can bind to CD4 on non-infected T4 cells (Chaplin, 1999, Med. Hypoth. 52:133-146). Thus, gp120 in infected individuals may induce immune system attack on non-infected T4 cells as well as infected cells (Chaplin, 1999, Med. Hypoth. 52:133-146). This would account for the observation that the majority of T4 cells are eliminated by late-stage HIV infection, despite the fact that only about 1 in 10,000 T4 cells is infected early in HIV infection and only about 1 in 100 T4 cells is infected in terminal AIDS (Chaplin, 1999, Med. Hypoth. 52:133-146). Circulating anti-gp120 antibodies produced by activated B cells can bind to gp120 on the surface of infected and non-infected T4 cells, resulting in cross-linking and activation of antibody dependent cellular cytotoxicity (ADCC) directed against T4 cells (Chaplin, 1999, Med. Hypoth. 52:133-146).

The gp120 polypeptide includes a superantigen binding region as well as regions involved in binding to CD4 and to the chemokine coreceptor (CCR). In particular, glycosylated, unglycosylated and heat denatured forms of gp120 include a superantigen (SAg) region (including portions of V4 (e.g., residues 392-434) and C2 (e.g., residues 261-272)) that appears to interact with immunoglobulins of the VH3+ gene family in B cells (Karray and Zouali, 1997, Proc. Nat'l. Acad. Sci. USA 94:1356-1360, particularly FIG. 3; Goodglick et al., 1995, J. Immunol. 155:5151-5159; U.S. Pat. No. 5,691,135). In addition specific arginine residues in V3 loop of gp120 appear to be involved in binding of gp120 to the chemokine coreceptor (CXCR4 and CCR5) (Wang et al., 1998, P.N.A.S. 95:5740-5745 and Lin et al., 2001, J. Virol. 75:10766-10778). Furthermore, binding of gp120 to CD4 appears to involve many amino acids with Asp368, Glu370 and Trp427 being of particular importance (Wyatt et al., 1998, Nature 393:705-711).

The depletion of T cells in HIV patients appears to stem in part from B-cell production of antibodies against the envelope protein (e.g., gp120) of the HIV rather than by direct infection with HIV (Yang et al., 1996, J. Virol. 70:5799-5806). Indeed, between 80-100% of the cell death associated with HIV infection occurs in uninfected T4 cells (Weinhold et al., 1989, J. Immunol. 142:3091-3097; Finkel et al., 1995, Nat. Med. 1:129-134). It is believed that when gp120 is shed from the virus, the protein becomes either free-floating in the bloodstream or is bound to the surface of uninfected cells, particularly T4 cells via the CD4 receptors (Mittler and Hoffman, 1989, Science 245:1380-1382; Wang et al., 1994, Eur. J. Immunol. 24:1553-1557; Finco et al., 1997, Eur. J. Immunol. 27:1319-1324; Kang et al., 1997, Eur. J. Immunol., 28:2253-2264). Uninfected but dying T4 cells have been observed by numerous researchers to be coated with virally produced gp120 protein and anti-gp120 antibody. Additionally, multiple in vitro and in vivo model systems demonstrate AIDS-like immune system collapse with just these two components (Mittler and Hoffman, Wang et al., Finco et al., Kang et al.). Also, clinical retrospective studies have shown that progression to AIDS is strongly correlated with the combination of high gp120 levels and high anti-gp120 antibody concentration (Skowron et al., 1997, AIDS 11:1807-1814).

As the T4 cell death characteristic (and causative) of AIDS involves both virally produced gp120 and host produced anti-gp120 antibody, both of which are necessary and neither of which are sufficient, immunomodulatory therapies designed to eliminate the anti-gp120 antibody response may prove highly beneficial.

Immunosuppression therapy has been employed for the treatment of a number of diseases. Immunosuppression may be used for medical conditions in which a triggering event elicits an immune response, causing unwanted or deleterious responses in the host. Accordingly, immunosuppression finds use in autoimmune disease management, transplantation protocols, allergy management, and the like.

The term "autoimmune disease" as used herein is defined as a disorder that results from immune responses that directly or indirectly target host cells or tissue. Autoimmunity is an inappropriate and excessive response to self-antigens. Examples include but are not limited to, Graves' disease, Type I-Diabetes mellitus, pemphigus, autoimmune hepatitis, Rheumatoid arthritis, and Systemic lupus erythematous.

Drugs currently used to treat autoimmune diseases are non-specific immunosuppressive agents, such as anti-inflammatory agents or drugs which can block cell proliferation or depress proinflammatory cytokines, and, moreover, due to their non-specific immunosuppression effects, run counter to the goal of maintaining immune function in the presence of an HIV infection.

It is desirable to suppress the immune system in a more specific way to control the response to self-antigens and theoretically "cure" the disease without down-regulating the entire immune system. Several specific immunotherapies have been hypothesized and tested in recent years, many of which are impractical or do not work in humans.

A need exists for alternatives to general immunosuppression for the treatment of pathogen-induced autoimmune conditions such as HIV pathogenesis (AIDS) and antibody-mediated autoimmune diseases in general. Of particular interest would be the development of an immunosuppression protocol that is able to selectively eliminate a specific antigen-reactive B cell population of a host's immune system and prevent the mistargeting and destruction of health.

In an attempt to reduce or eliminate specific B-cells, several groups have attempted to introduce toxic antigens (e.g., ricin- or radio-labled antigens) that would destroy only B-cells producting that antibody. However, significant vascular leakage and non-specific cell necrosis was observed (Baluna, et al. (1999) P.N.A.S. 96:3957-3962, Baluna, et al. (1999) J. Immunotherapy 22:41-47, Soler-Rodriguez, et al. (1993) Exp. Cell Res. 206:227-234, and "Medical Aspects of Chemical and Biological Warfare" Office of the Surgeon General (1997) Chapter 32, Franz and Jaax). Fusions of antigen and toxin have also failed to exhibit the requisite specificity to be administered in the presence of a preexisting antibody response. (Ada et al. (1969) Nature 222:1291-1295.

Interaction of antibodies with traditional antigen-toxin fusions is a key concern as antigen bound antibodies are internalized by macrophages and dendritic cells and this uptake of the bound complex is expected to delete these and other key antigen-presenting components of the patient's immune system along with the targeted B cells. Given the extreme toxicity of these compounds it is imperative that they only target the intended B cell population, as a single misdirected drug molecule will kill a "bystander" cell. The present invention was designed as a two-component fusion toxin system with independent targeting mechanisms that must be correctly activated and overlap on the target cell population to deliver their two interdependent toxin moieties.

GENERAL OVERVIEW

Described herein are compositions and methods for selective reduction or elimination of specific B-cell populations. In particular, multi-component B-cell clonal toxins are described. Each component of the multi-component system comprises a targeting domain and a toxin domain, for example a fusion of such molecules. Preferably, the toxin domains are interdependant. I.e. they are not toxic until they interact with each other and/or are processed inside the target cell. Thus, only cells that react with both of the targeting domains will internalize a fully functional toxin.

The multi-component nature of the compositions described herein provides specificity for target cells not previously achieved with traditional antigen-toxin fusions. Single component toxins, and most multi-component toxins, are not sufficiently specific. Systems involving two toxin components (even when produced in separate cell lines) associate tightly when contacted with each other, thereby losing independent targeting and resulting in insufficient specificity and toxicity to non-target cells. For example, multi-component toxins comprised of Diphtheria toxin A and B chains spontaneously and stably reassociate to form heterodimeric complexes; also multi-component toxins comprised of Anthrax Protective Antigen (APA) and any toxin A chain containing an Anthrax Lethal Factor or Oedema Factor leader sequence has, in effect, any one targeting domain as the leader sequence will bind to the activated APA regardless of any other targeting sequences on that toxin component (U.S. Pat. Nos. 4,664,911, 5,677,274, and 5,830,478).

In contrast to these previous antigen-toxin fusions, the molecules described herein are toxic only when combined and correctly processed within the targeted B-cell. In particular, the interdependent toxin domains of the multi-component toxins described herein are blocked from association with each other and from activation until they have been proteolytically processed and/or activated within the target cells. Thus the compositions and methods described herein do not result in unwanted destruction of macrophages, dendritic cells, and other key antigen presenting components of the patient's immune system even when simultaneously co-administered.

Although exemplified herein with respect primarily to HIV clade C gp120 it will be understood by the skilled artisan that the present invention is not limited to such embodiments described below and may be extended to any antigen that a B-cell may react to. It will be apparent to those of skill in the art that variations may be generated by simply using a different antigen segment (i.e. ACh receptor for Myasthenia Gravis, etc) for a different target B cell population. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 (SEQ ID NO:1) depicts an exemplary amino acid sequence of an Indian (clade C) consensus HIV gp120 protein with nine mutations to increase suitability. The location of preferred amino acid modifications that inhibit CD4 binding (D365K and E367R, corresponding to D368K and E370R in the U.S. clade B consensus sequence following the original Gallo notation), chemokine coreceptor (R313A, corresponding to R335A in the U.S. sequence), and SAg binding (392-394 and 415-417, corresponding to 395-397 and 418-420 in the U.S. sequence) are indicated in bold and underline. An alignment of gp120 proteins from various HIV isolates is shown in U.S. Provisional Application No. 60/520,520, the disclosure of which is incorporated by reference in its entirety herein, equivalent alignments may be found at www.hiv.lanl.gov/content/index.

FIG. 2 (SEQ ID NO:2) depicts the amino acid sequence of an exemplary modified IL-4 segment. The location of a preferred amino acid modifications to maintain binding to (and internalization by) the IL-4 receptor while eliminating signaling through said receptor (Y124D, bold and underlined) is indicated.

FIG. 3 (SEQ ID NO:3) depicts the amino acid sequence of an exemplary modified Anthrax Protective antigen segment the requires proteolytic processing prior to providing either binding or translocation to the enzymatically active toxin portion. Amino acids 1-18 (bold and underlined) are non-structural leader sequences that may be deleted. Amino acids 1-167 (shown in bold) are proteolytically removed by furin to oligomerize and provide binding and translocation for an enzymatically active toxin portion. Amino acids 607-736 (underlined) are the wild type receptor-binding domain and are preferably deleted when used as the toxin component of the molecules described herein.

FIG. 4 (SEQ ID NO:4) depicts the amino acid sequences of an exemplary modified Diptheria toxin A chain (enzymatically active) fragment requiring a protelytically processed cofactor and acidic environment prior to binding and/or translocation.

FIG. 5 (SEQ ID NO:5) depicts the amino acid sequence of an exemplary gp120-B-cell specific targeting sequence of the present invention. The B-cell specific targeting sequence includes and acid-dependant polycationic octahistidine tract (amino acid residues 1-8); a linker segment (amino acid residues 9-14), a diphtheria toxin A chain as shown in FIG. 4 (amino acid residues 15-207, inclusive), a proteolytically cleavable linker (amino acid residues 208-220), and a modified HIV gp120 sequence (amino acid residues 221-725).

FIG. 6 (SEQ ID NO:6) depicts the amino acid sequence of another exemplary gp120-B-cell specific targeting sequence of the present invention. The B-cell specific targeting sequence includes an anthrax protective antigen segment as shown in FIG. 3 (amino acid residues 1-574, inclusive); a linker sequence (amino acids 575 to 580, inclusive); and a modified IL-4 sequence (amino acid residues 581-709, inclusive).

MULTI-COMPONENT CLONAL TOXINS

In describing the present invention, all technical and scientific terms used herein have the same meaning as commonly understood to one of ordinary skillin the art unless defined otherwise as indicated below.

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, Proteins: Structures and Molecular Properties (W.H. Freeman and Company, 1993); Nelson L. M. and Jerome H. K. HIV Protocols in Methods in Molecular Medicine, vol. 17, 1999; Sambrook, et al., Molecular Cloning: A Laboratory Manual (Cold Spring Harbor Laboratory, 1989); F. M. Ausubel et al. Current Protocols in Molecular Biology, Greene Publishing Associates and Wiley Interscience New York; Goldsby et al., Kuby Immunology, 4th ed. (Freeman and Company, New York, 2000); and Lipkowitz and Boyd, Reviews in Computational Chemistry, volumes 1-present (Wiley-VCH, New York, N.Y., 1999).

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

DEFINITIONS

In describing the present invention the following terms will be employed and are intended to be defined as indicated below.

The terms "polypeptide" and "protein" are used interchangeably herein to denote any polymer of amino acid residues. The terms encompass peptides, oligopeptides, dimers, multimers, and the like. Such polypeptides can be derived from natural sources, recombinant sources, or directly synthesized and may incorporate natural or synthetically produced amino acid analogues (homoserine, norleucine, etc.) as well as the 20 common amino acids. The terms also include post expression modifications of the polypeptide, for example glycosylation, acetylation, phosphorylation, etc.

The terms "fusion protein" and "fusion molecule" refer to a molecule in which two or more subunit molecules are linked, typically covalently. The subunit molecules can be the same chemical type of molecule or can be different chemical types of molecules (e.g., polypeptide and polysaccharide).

By "targeting moiety" or "targeting domain" is meant a molecule that binds to a specific binding partner. For example, a gp120-targeting domain as described herein binds to gp120-specific B-cells and to anti-gp120 antibodies. Similarly, an IL-4 targeting domains described herein binds to B-cells and T4 cells. One or more of the same or different targeting domains may be used in the compositions and methods described herein. Furthermore, the targeting domain may be a naturally occurring molecule, for example a naturally occurring polypeptide. Because many naturally occurring genomes are in a state of constant and rapid flux (e.g., HIV genome), there may be a high degree of variability between the sequences of gp120 from differing isolates. It is readily apparent that the terms encompass poly peptides from any of the identified HIV isolates and subtypes of these isolates. One of ordinary skill in the art in view of the teachings of the present disclosure and the art can determine corresponding regions in other HIV variants and strains.

In addition the term "targeting domain" includes molecules having additional modifications as compared to the native molecule (e.g., sequence), such as additional internal deletions, additions, and substitutions. These modifications may be deliberate, as through site-directed mutagenesis, or may be non-intentional, such as through naturally occurring mutational events (antigenic drift). Thus, as shown in FIGS. 1 and 2, the targeting domains may include modifications that inhibit binding or internalization to known binding partners (e.g., CD4 in the case of gp120 and internalization by the IL-4 receptor in the case of IL-4) but do not inhibit binding to the targeted antibodies or cells (e.g., B-cells).

The term "binding region antigen-selective" or "BRA" refers to a targeting domain that binds to a particular, specific antigen-binding region of an antibody (membrane bound B-cell receptor for antigen or soluble antibody). Preferably the BRA does not bind to other receptors on the target cell or other cells. Similarly the term "binding region cell lineage-selective" or "BRL" refers to a targeting domain that binds to a particular lineage specific receptor displayed on the surface of the target cell (e.g., IL-4 receptors on the surface of B-cells). Preferably the BRL does not bind to other receptors on the target cell or on other cells.

By "toxin moiety" or "toxin domain" is meant a molecule that exhibits toxic effects on a cell, particularly the reduction or elimination of antibody production by a B-cell, either by inhibition of normal cellular function, initiation of apoptosis, or cell death. A toxin domain may be toxic alone when properly processed by the target cell or may be toxic only in combination with one or more additional molecules (e.g., another toxin domain). When two or more toxin domains must interact in order to be toxic the individual domains may be referred to as "toxin A chain (TAC)" and "toxin B chain (TBC)".

Toxin domains may be naturally occurring molecules or functional fragments thereof. Alternatively one or more toxin domains may include additional modifications as compared to the native molecule (e.g., sequence) such as additional internal deletions, additions, and/or substitutions. For instance native receptor binding regions may be removed (FIG. 3). In addition, a toxin domain may require proteolytic processing and/or specific environmental conditions (e.g., acidic environment) prior to becoming toxic.

The term "interdependant", when used in reference to toxin domains refers to toxin moieties which when administered by themselves to a host exhibit little or no toxicity and little to no interaction with each other regardless of whether the administration occurs separately, simultaneously, or singly.

The term "toxin interacting region" or "TIR" refers to regions of the toxin domains that interact with each other, for example by causing dimerization of separate toxin domains to each other and/or translocation of a toxin domain into an activating region of the target cell.

As used herein a "target cell" is any B-cell capable of producing antibodies that can bind to a specified antigen (in vitro or in vivo). Thus a target cell can be a B-cell producing any unwanted antibodies, for example anti-AChR antibodies in myasthenia gravis or anti-gp120 antibodies in HIV+ individuals.

As used herein, "about" means within plus or minus five percent of a number. For example, "about 100" means any number between 95 and 105.

The term "moiety" is used broadly to refer to any atom, molecule, chemical, compound, composition, group, isotope or aggregate. In particular embodiments, a "moiety" may be any atom, molecule, chemical, compound, composition, group, isotope or aggregate that exhibits a selected function, activity, functionality or property.

DETAILED DESCRIPTION OF ILLUSTRATIVE EMBODIMENTS

It will be understood by the skilled artisan that the present invention is not limited to the particular embodiments described below. Variations of the particular embodiments may be made and still fall within the scope of the appended claims.

The present disclosure relates molecules that are toxic to a sub-population (clonal population) of B-cells that proliferate to produce antigen-specific antibodies upon binding of said antigen. The clonal toxins include at least first and second fusion molecules, where each fusion molecule comprises a targeting domain and a toxin domain. The targeting domain of each fusion molecule provides for selective binding to and internalization of the molecule by separate target receptors while the toxin domains, together, interact once internalized to inhibit cellular function or to kill the target B-cell.

The overall size of the clonal toxin component molecules may vary, depending on the specific components from which it is made, so long as the molecules are of sufficient size to be recognized and internalized by the target cell following binding by the target domains. The molecular weight of each clonal toxin component molecule is generally at least about 40 kD, usually at least about 80 kD, and may be as great as 250 kD or greater, but usually does not exceed about 110 kD.

Certain embodiments of the clonal toxins of use in the disclosed methods and compositions may be described by the formula (beginning from either the N-terminus or C-terminus of the fusion protein component):

Nomenclature:
[TAC]=Toxin A Chain
[TBC]=Toxin B Chain
[TIR]=Toxin Interaction Region
[BRA]=Binding Region Antigen-Selective
[BRL]=Binding Region Cell Lineage-selective
([BRA]L)nP([TAC])n2 (molecule 1) and ([BRL]L)n3P([TBC])n4 (molecule 2)
or
([BRL]L)nP([TAC])n2 (molecule 1) and ([BRA]L)n3P([TBC])n4 (molecule 2)
wherein
[BRA] and [BRL] are the targeting moieties;
L is a bond or a linking group;
P is a proteolytically cleavable linker group;
[TAC] and [TBC] are the toxin component moieties;
n, n2, n3, and n4 are integers from 1 to 50, and usually from 1 to 5.

The targeting moiety, toxin moiety and/or linking group of each molecule are covalently attached to each other, although non-covalent attachment via ionic interaction, hydrogen bonding, van der Waals interaction, or any other form of binding are within the scope of the invention. The skilled artisan will realize that the targeting moieties ([BRA] and [BRL]) and the toxin moieties ([TAC] and [TBC]) are the active components of the clonal toxin and in certain embodiments of the invention the targeting moiety and toxin moiety may be directly covalently attached by any known method, including but not limited to construction and expression of a gene encoding a fusion protein comprising the sequences of [BRA][TAC] and [BRL][TBC]; the chemical synthesis and covalent cross-linking of [BRA] or [BRL] units with [TAC] or [TBC] units; the purification and/or truncation of [BRA], [BRL], [TAC], and [TBC] followed by covalent cross-linking; or any other known method of producing chimeric and/or fusion proteins.

The skilled artisan will realize that the values of "n", "n2", "n3", and "n4" are not limiting and that any number of targeting moieties may be attached to any number of toxin moieties within the scope of the invention with any arrangement (linear, branched, multimeric, etc.). The above formula is exemplary only and other combinations of toxin and targeting moieties, not described by the above formula, are contemplated within the scope of the invention. If preferable to disassociate the component moieties upon internalization of the construct proteolytically or reductively labile linkers "P" may be used. Such labile linkers are well known to those skilled in the art.

Targeting Domains—[BRA] and [BRL]

Multi-component clonal toxins of use in the disclosed methods and compositions comprise at least two targeting domains. In various embodiments, the [BRA] targeting moiety is capable of selectively, preferably specifically binding to the antigen-binding region of a receptor displayed on the surface of the specific target antigen-reactive B cells. In preferred embodiments, the [BRA] targeting moiety provides for internalization of the antigen-selective component of the clonal toxin by the target cell(s) and may be a polypeptide, polysaccharide, nucleic acid, etc. Preferably, [BRA] is any moiety that binds to the antigen-binding region of an antibody displayed on the surface of the target cell(s) and not to the CD4, chemokine coreceptor, or superantigen binding or other regions or receptors. More preferably, the clonal toxin is internalized into target cells solely upon binding to the Fab segment of an immunoglobulin receptor on the surface of the target B cells. In certain embodiments of the invention, the [BRA] targeting moiety is a modified version of the HIV gp120 antigen or an antibody binding fragment or mimetic thereof, e.g. a synthetic hapten that includes the epitope recognized by the paratope of a surface displayed antibody of the gp120-reactive target cell(s). It is within the scope of the invention to purify, either as a gene sequence or protein, the antigen directly from the patient (as in the case of variant forms of patient specific HIV gp120) and directly couple this material (or its gene product from translation) to either [TAC] or [TBC] for use as the [BRA] targeting sequence.

The [BRA] targeting moiety will generally include one or more domains (e.g., epitopes) for interaction and binding to a surface receptor on the target cell, for example an anti-gp120 antibody. As described below, the targeting moiety may also include regions that may be modified and/or participate in a linkage to the other components of the clonal toxin, such as the toxin moiety or linker. Preferably, attachment of the [BRA] targeting moiety to a toxin moiety and/or linker group does not adversely affect the ability of the targeting moiety to bind to its corresponding receptor on the target cell(s).

In preferred embodiments of the gp120-specific invention, the [BRA] targeting moiety comprises part or all of the gp120 protein that has been modified to decrease or eliminate superantigen binding, chemokine coreceptor binding, and CD4 binding. In a non-limiting example, CD4 binding is removed by substituting a lysine residue for Asp365 and an arginine residue for Glu367, while superantigen binding is eliminated by substituting alanine residues for Leu392, Phe393, Asn394, Thr415, Leu416 and Pro417, and chemokine coreceptor binding is inhibited by substituting a glycine residue for the arginine in the gpgraf V3 loop tip. The skilled artisan will realize that the exemplary substitutions are not limiting. In different variants of the gp120 protein, the native residues at these positions may differ from those listed above. In alternative embodiments of the invention, additional or different amino acid residues in the gp120 sequence may be substituted. The skilled artisan will realize that a wide variety of non-conservative substitutions are possible, the only requirement being that the [BRA] targeting moiety binds to target cells exhibiting specific antigen binding, preferably without binding to non-target cells.

In various gp120 specific embodiments of the invention, the [BRA] targeting moiety may be selected to mimic the sequence of an endogenous HIV gp120 protein, for example as found in a patient infected with HIV. Methods for obtaining and sequencing gp120 variants and/or HIV genes encoding gp120 from patient samples are known in the art. In certain embodiments, the gp120 sequence found in a patient may vary over the course of infection with HIV. It is within the scope of the present invention to vary the sequence of the targeting moiety accordingly, to resemble whatever gp120 sequences are found in a patient. In alternative embodiments, the [BRA] targeting moieties may be selected to mimic one or more gp120 sequences known to occur in a given sub-population of individuals and/or a given geographic region. All gp120 sequence variants known to occur in a sub-population and/or geographic region may be represented in a single clonal toxin to be administered to patients in that sub-population and/or region.

Deletion of the SAg binding site via non-conservative mutations in the HIV gp120 sequence minimizes non-specific B cell internalization and inactivation by the clonal toxin. This preserves a greater range of immune function in the treated patient and reduces competition for the clonal toxin by pre-existing superantigen gp120 binding antibodies in circulation. There is a resulting decreased rate of internalization of antigen/antibody complexes and killing of macrophages. Additionally, deleting the CD4 and chemokine coreceptor binding abilities of the clonal toxin drastically reduce side-effects and required dose by preventing binding and uptake by T4 cells. These clonal toxin characteristics advantageously reduce the amount of clonal toxin required for treatment, increase plasma half-life of the clonal toxin and decrease the number of deleterious side-effects of administration, without compromising the efficacy of the clonal toxin at reducing or eliminating the immune system dysfunction characteristic of HIV infection.

Antigens can be identified based on the ability to bind to the antibodies using any of the variety of methods well know in the art including, but not limited to, radioimmunoassays (RIA), direct and indirect enzyme-linked immunosorbent assay (ELISA), direct, indirect and indirect complement amplified immunofluorescence, immunoblotting, such as Western blotting and also the method of surface plasmon resonance.

Therefore, a skilled artisan realizes that any macromolecule, including virtually all proteins or peptides, can serve as antigens. Furthermore, antigens can be derived from recombinant or genomic DNA. Furthermore, one skilled in the art realizes that the present invention is not limited to the use of the entire nucleic acid sequence of a gene or genome. It is readily apparent that the present invention includes, but is not limited to, the use of partial nucleic acid sequences of more than one gene or genome and that these nucleic acid sequences may be arranged in various combinations to elicit the desired binding.

In various embodiments, the [BRL] targeting moiety is capable of selectively, preferably specifically binding to a B-cell lineage specific receptor displayed on the surface of all B cells. In preferred embodiments, the [BRL] targeting moiety provides for internalization of the second clonal toxin component by all B-cells and not by macrophages or dendritic cells. Preferably, [BRL] is any moiety that binds to a B cell specific marker displayed on the surface of the target cells and not to the surface markers of either macrophages or dendritic cells (i.e. IL-4 receptors or similar receptors present on B cells but not macrophages or dendritic cells). More preferably, the clonal toxin is internalized into target cells solely upon binding to the B cell lineage specific marker on the surface of the target B cells. In certain embodiments of the invention, the [BRL] targeting moiety is a modified version of the Interleukin-4 cytokine hormone or mimetic thereof, e.g. a synthetic hapten.

The [BRL] targeting moiety will generally include one or more domains for interaction and binding to a surface receptor on the target cell, for example an IL-4 receptor (or ligands of CD19, CD20, CD22, CD79, CD124, CD138, IL-6R, IL-7R, IL-9R, or IL-13R, etc.). As described, the targeting moiety may also include regions that may be modified and/or participate in a linkage to the other components of the clonal toxin, such as the toxin moiety or linker. Preferably, attachment of the [BRL] targeting moiety to a toxin moiety and/or linker group does not adversely affecting the ability of the targeting moiety to bind to its corresponding receptor on the target cell(s).

As used herein, a target cell may be any B cell capable of producing antibodies that can bind to a specified antigen under in vivo conditions. In preferred embodiments of the gp120 specific compound, the target cell, once activated, would produce antibodies that can bind to gp120 attached to the surface of T4 cells.

Clonal toxin component molecules include at least one targeting moiety, but may alternatively include a plurality of such moieties. In alternative embodiments, the multiple targeting moieties may be the identical or may be different, such that a given clonal toxin component may include two or more copies of the same targeting moiety and/or may contain two or more different targeting moieties. The number of targeting moieties incorporated into a single clonal toxin may be as high as 50 or more, but will generally not exceed about 8 and in many embodiments will not exceed about 5. Where a plurality of targeting moieties are present in the clonal toxin, they may be arranged in any manner, e.g. sequentially, in a branched format at the termini of a branched linker, attached to the ends of individual linkers, etc. The manner in which the targeting moieties are arranged may depend, in part, on the manner by which the clonal toxin is prepared, for example as a fusion protein, by chemical synthesis, by covalent cross-linking, by in vivo or in vitro translation or any other method known in the art.

Toxin Domains—[TAC] and [TBC]

The toxin domains ([TAC] and [TBC]) of each clonal toxin component molecule are interdependent but non-interactive. By this it is meant that the toxin moieties, when administered by themselves to a host without an attached targeting moiety, exhibit little or no toxicity and little to no interaction with each other regardless of whether the administration occurs separately, simultaneously, or singly. Thus, when administered by itself to a host the toxin moiety produces negligible, if any, cellular internalization or observable symptoms. Preferably, when administered by itself in an amount ranging from about 10 to 100 mg to a human having a weight ranging from about 50 to 75 kg, each toxin moiety exhibits little, if any, toxic effect, even if administered in conjunction with the other toxin moiety. As such, the toxin moiety is generally one that exhibits low or no non-specific binding when administered by itself to a human. Additionally, the toxin moieties demonstrate little to no affinity for each other until bound to (and internalized) by the target cells and appropriately processed.

The toxin moieties also must efficiently inactivate a target cell upon entry of the enzymatically active ([TAC] component) into the cytosol. By inactivate is meant that the [TAC] toxin moiety inhibits the cell from producing antibodies. In many embodiments, the [TAC] toxin moiety is one that efficiently kills the target B cell(s). By efficiently kills is meant that from 1 to 50 [TAC] toxin moieties are capable of killing a cell upon entry of said toxin moiety into the cytosol of that cell. In many embodiments, the [TAC] toxin moiety is chosen such that one to two toxin moieties are capable of killing the target cell. The [TAC] toxin moiety exhibits efficient toxicity to target cells in the presence of activated [TBC] toxin moiety even though it is administered as an inactive component of the clonal toxin by itself. One example of such an enzymatically active and efficient [TAC] toxin moiety is the Diphtheria toxin A chain which must interact with a translocating moiety to internalize into its target cell, for it has no translocation ability of its own.

In various embodiments, the [TBC] toxin moiety is capable of translocating another protein chain (e.g toxin component [TAC]) from a lysosome/proteolysosome into the cytosol of a target cell after being proteolytically activated. In such embodiments, binding of a clonal toxin component containing the [TBC] toxin moiety to a corresponding receptor (e.g., antibody or B cell lineage-specific receptor) on the surface of a target B cell may be followed by internalization of the clonal toxin component containing toxin moiety [TBC] into a lysosome/proteolysosome which provides the necessary environment for proteolytic processing of the toxin and acid dependant translocation of the [TAC] toxin moiety. Since preferred examples of [TAC] toxin moieties only exhibit cell toxicity when delivered to the cytosol of target cells, the [TBC] toxin moiety preferably is efficient in translocating [TAC] toxin moieties from a lysosome/proteolysosome to the cytosol.

Non-limiting examples of toxins that may be employed as the [TAC] toxin moieties of B cell clonal toxins include receptorless and translocation deficient forms of the enzymatically active chains of diptheria toxin, *Pseudomonas* exotoxin E, pertussis toxin, *Yersina pestis* toxin, abrin, gelonin, ricin, verotoxin, Shiga toxin, Shiga-like toxin, pokeweed antiviral protein, anthrax toxin lethal factor or oedema factor, trichoanguin, mistletoe toxic lectin-I, saporin, *H. pylori* vacuolating toxin, Botulinum neurotoxin, cholera toxin, LT toxin, C3 toxin, tetanus toxin, and any other type-I or type-II ribosome inactivating toxins. Analogs of these toxins containing artificially added reactive cysteine residues for the attachment of patient-derived antigen ([BRA]) are also included within the scope of the invention. These and other toxins of use in the claimed compositions and methods are known in the art and toxin amino acid sequences may be obtained from publicly available databases (e.g., http://www.ncbi.nlm.nih.gov/). As discussed above, toxin moieties may be produced by any method known in the art, such as cloning into expression vectors and in vitro or in vivo translation, peptide synthesis, purification of natural proteins or peptides, etc.

Non-limiting examples of biologically acceptable toxins that may be employed as the [TBC] toxin moieties of B cell clonal toxins include receptorless and translocationally active chains of Anthrax toxin Protective Antigen, Clostridium Perfringens toxin B chain, or any similar B chain from an A+B configuration type-II ribosome inactivating toxin requiring processing for association of the A and B units, as well as any other translocation domain displaying equivalent characteristics.

Multi-component toxins may have a toxin domain linked to an antigen-mimetic construct and a toxin translocation domain linked to a lineage-specific targeting moiety, such that the full set of toxin components required for efficient cytotoxicity only occur in the proteolysosomal compartment of B cells reactive against the specified antigen. In a non-limiting example, such a two-component system may involve administering the enzymatically active toxin domain (A chain) of diptheria toxin (DTA) linked to a non-specific binding deficient gp120 analog targeting moiety, and the translocation domain (Protective Antigen) of Anthrax toxin linked to a different targeting moiety that is B cell lineage specific (such as an analog of human IL-4). The two components would be independently taken up into gp120-reactive B cells and combined in a proteolysosome, resulting in translocation of the enzymatically active toxin chain (DTA) into the target cell cytosol. Use of multi-component toxins would decrease the probability of toxicity to any cells other than the targeted B cell sub-population and would further reduce the incidence of side effects of the clonal toxin, thus markedly increasing the therapeutic index of such compounds. Toxin Interaction Regions—[TIR]

As noted above, the interdependant toxin domains described herein interact with each other via one or more toxin interaction regions (TIR). Because native toxic polypeptide subunits exhibit high affinity for each other unblocked subunits will form intact and toxic dimers in serum or on cell surfaces even when administered separately. This is documented by publication within U.S. Pat. No. 4,664,911 that injection of mice with nontoxic ricin A chain followed 4-8 hours later by injection with non-toxic ricin B chain produces ricin-induced death. This indicates that, even when administered separately, unblocked A and B chains from protein toxins spontaneously form active and toxic heterodimers. Examples of [TIR]s with processing requirement dependant blocks to activation include the proteolytic requirement of Anthrax and Clostridial Protective Antigens ([TBC]) such that they cannot oligomerize and form an active translocation complex until a 20 Kda fragment is proteolyzed by furin or similar enzymes. An additional example is the use of a polyhistidine tract to bind to activated APA—while polycationic tracts are known to bind to and induce translocation by APA the polyHistidine tract does not take on the appropriate charge characteristic outside of the acidic proteolysosome. This acid requirement of the polyHistidine [TIR] provides a significantly enhanced safety and targeting benefit by providing holotoxin complexation only within a proteolysosome environment. Linking Moiety—L The targeting and toxin moieties of the clonal toxins may be joined together through a linking moiety L, where L may be either a covalent bond or a linking group. Where linking groups are employed, such groups are typically chosen to provide for covalent attachment of the targeting and toxin moieties through the linking group in a manner that preserves the activities of the targeting and toxin moieties. Linking groups of interest may vary widely depending on the natures of the component parts of the clonal toxins, the manner in which the clonal toxins are produced, etc. The linking group, when present, should preferably be biologically inert. A variety of linking groups are known in the art and find use in the subject clonal toxins. The linker groups are typically small, generally at least about 100 daltons, usually at least about 250 daltons and may be as large as 2 kD or larger, but generally will not exceed about 800 daltons and usually will not exceed about 450 daltons.

The skilled artisan will realize that any linker group known in the art may be used in the practice of the claimed invention, so long as it may be used to join toxin moieties and targeting moieties without significantly interfering with their functional properties.

Fabrication and Purification of Clonal Toxins

Clonal toxins may be fabricated using any techniques known in the art. For example, where all of the components of the clonal toxin are peptides or proteins, the toxin may be prepared as a fusion protein, where a polynucleotide encoding each of the components of the clonal toxin may be prepared, e.g. via recombinant techniques, and then expressed in a suitable expression host cell. Methods of making fusion proteins are well known to those of skill in the art (e.g., U.S. Pat. Nos.: 4,664,911; 5,876,943; 5,863,745; 5,843,726; 5,837,825; 5,837,816; 5,834,267; 5,747,659; 5,733,760; 5,728,552; 5,696,237; 5,674,980; 5,672,683; 5,580,757; 5,580,756; 5,554,526; 5,532,339; 5,529,909; 5,521,288; 5,496,924; 5,378,806; 5,334,532; 5,180,811; 5,130,248; 5,130,247; 5,116,750; 5,100,788; 5,093,241; 5,087,563; 5,082,927; 5,013,653; and 4,973,551; the disclosure of each of which is incorporated by reference).

Alternatively, the clonal toxins may be constructed from their individual components. The components can be covalently bonded to one another through functional groups, as is known in the art, where such functional groups may be present on the components or introduced onto the components using one or more steps, e.g. oxidation reactions, reduction reactions, cleavage reactions and the like. Functional groups that may be used to covalently bond the components together include hydroxyl, sulfhydryl, amine groups and the like, as discussed above. The particular portion of the different components that are modified to provide for covalent linkage will be chosen so as not to adversely interfere with that component's activity. For example, for the targeting moiety a modification site that does not affect the target receptor binding activity will be selected, such that receptor binding activity is preserved. Where appropriate, certain residues on the components may be protected using blocking groups, as is known in the art, (e.g. Green & Wuts, Protective Groups in Organic Synthesis, John Wiley & Sons, 1991).

Analogs of native proteins or peptides of use in the claimed methods and compositions will be greater than 70%, preferably greater than 85%, more preferably greater 98%, in some cases 99% or more identical in amino acid sequence to the corresponding native protein or peptide, where representative native protein sequences for gp120 are determined by their CD4 and chemokine coreceptor binding ability or their direct amplification from any of the variant HIV strains. Sequences having lesser degrees of similarity but comparable biological activity are considered to be equivalents. In determining nucleic acid sequences of use, all subject nucleic acid sequences capable of encoding the same amino acid sequence are considered to be equivalent to a reference nucleic acid, regardless of differences in codon usage.

Additional details of methods of use for fabrication of clonal toxins in specific embodiments of the invention are disclosed below.

Protein and Peptide Purification

Certain embodiments may involve purification of one or more gp120 proteins, toxin proteins or peptides or analogs thereof. Protein purification techniques are well known to those of skill in the art.

In addition, it falls within the scope of this invention to provide for molecules without a [BRA] and to directly purify genes or protein from the patient in question for conjugation as a patient-specific [BRA] through reactive cysteines or any other coupling method. Such patient derived material may be purified and amplified via standard PCR and molecular biology techniques if the target is a gene from the patient in question. In the case of isolating antigen from the patient, as in the case of patient specific gp120, an effective collection of such antigens can be obtained by passing the serum fraction of blood over a column containing the respective antibody or other affinity agent (such as human CD4) chemically coupled to a matrix. Antigen specific to the antibody will be retained on the column while unrelated material passes through. The retained antigen then can be collected by elution from the column using suitable eluting agents, for example, acidic buffers or chaotropic agents. It should be noted that the isolated antigen is not homogeneous, nor screened for cross-reactivity. As a result, the possibility exists for cross-reaction with other related antigens and thus the deletion of an overly wide range of B cell reactivity.

Peptide Synthesis

In some embodiments, smaller peptides of about 100 amino acids or less comprising part or all of a gp120 or toxin sequence may be synthesized in solution or on a solid support. Various automated peptide synthesizers are commercially available and can be used in accordance with known protocols (e.g., Stewart and Young, 1984; Tam et al., 1983; Merrifield, 1986; and Barany and Merrifield, 1979, each incorporated herein by reference). Short peptide sequences, or libraries of overlapping peptides, usually from about 6 up to about 35 to 50 amino acids, which correspond to selected regions of the clonal toxin protein, can be readily synthesized and then conjugated together. Alternatively, recombinant DNA technology may be employed. Expression of cloned sequences is preferred in embodiments where clonal toxin peptides of greater than about 50 amino acids in length are desired.

Nucleic Acids Encoding Proteins or Peptides

Nucleic acids according to the present invention may encode part or all of a multi-component clonal toxin sequence. In preferred embodiments, the nucleic acid would comprise complementary DNA (cDNA) sequences. Nucleic acids may be based in whole or in part on known cDNA and/or genomic sequences encoding gp120 and/or toxin proteins or peptides (see, e.g. http://www.ncbi.nlm.nih.gov/). Alternatively, HIV strains may be isolated from patients and nucleic acids encoding gp120 recovered from the virus. Replacement of native codon sequences with codons encoding the same amino acids that have been optimized for expression in a specific host organism may occur using standard molecular biology techniques. Changes designed to substitute selected amino acids for a native sequence, e.g. in the CD4 and/or SAg binding sites of gp120, may be effected using known site-specific mutagenesis techniques or any other method known in the art.

Methods of combining coding sequences from two or more different proteins or peptides are well known in the art.

Applications

The subject clonal toxins find use in methods of selectively killing a specific antigen reactive B cell population, but sparing those B cells that bind other antigens as well as non-B-cells. In certain embodiments, a target B cell which displays an antigen binding receptor, e.g. antibody, on its surface that binds to the targeting moiety of the clonal toxin is contacted with the clonal toxin under conditions sufficient for binding and subsequent internalization of the clonal toxin to occur, e.g. under physiological conditions. Contact is achieved using any convenient protocol. For example, where contact occurs in vitro, an effective amount of the clonal toxin may be introduced into the environment of the target B cell, e.g. by addition to a container that houses the target B cell and the like. Likewise, where contact occurs in vivo, the clonal toxin may be contacted with the target B cell by administering the clonal toxin to the host animal, where administration may be oral, buccal, rectal, parenteral, intraperitoneal, intramuscular, intradermal, transdermal, intracheal, via aerosol to the lungs, etc., administration. In many embodiments, administration is via injection, e.g. intravenous or intramuscular.

As the toxin moiety of the subject clonal toxins is efficient, the target antigen-reactive B cell need be contacted with only a small number of complete clonal toxin molecules (both molecule 1, [BRA][TAC] OR [BRL][TAC], and molecule 2, [BRL] [TBC] OR [BRA] [TBC]), where the number that is contacted with and sufficient to kill the target B cell is at least 1, and may be as high as 20 or more, but generally does not exceed 5. As mentioned above, contact is carried out under conditions sufficient for binding of the targeting moiety to the surface receptor in an antigen-specific or B cell-lineage dependant manner (as opposed to a non-specific manner) and subsequent toxin molecule internalization to occur. At a minimum, the conditions under which contact occurs are those that are sufficient to maintain viability of the target B cell and not induce premature disaggregation of the toxin moiety. As such, conditions of interest include: physiological conditions, cell culture conditions and the like.

As described above, the subject invention provides a method of selectively killing a target antigen-reactive B cell via antigen-specific and B cell lineage specific binding rather than antigen-specific or B cell lineage specific means. Also provided by the subject invention are methods of selectively eliminating substantially all of the members of one or more clonal B cell populations (e.g. those that react with the HIV gp120 antigen(s) on the B cell toxin in a non-SAg dependant manner). By substantially all of is meant at least 75, usually at least 85 and more usually at least 90% of the members of an antigen-based gp120-reactive B cell population. By selectively killing is meant that, in a complex mixture of distinct B cell populations, i.e. B cells that recognize different antigens, contact of the mixed B cell population with the B cell clonal toxin results in killing of all of or substantially all of the target B cell antigen-based (i.e. gp120-reactive) population(s) but little or no killing of B cells that are not a member of the target B cell population(s) (or those that bind to HIV gp120 solely through the superantigen binding framework of native gp120). Where killing of non-target B cells occurs, the percentage of non-target B cells that are killed as compared to the total B cell population of the complex mixture does not exceed about 3, usually does not exceed about 1 and more usually does exceed about 0.1%.

Formulations and Routes for Administration to Patients

In certain embodiments, the clonal toxin may be used for therapeutic treatment of medical conditions, such as antibody-based autoimmune diseases, immune responses to gene therapy agents, or AIDS. Where clinical applications are contemplated, it may be necessary to prepare pharmaceutical compositions in a form appropriate for the intended application.

Aqueous compositions of the present invention comprise an effective amount of the multi-component clonal toxin, dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the clonal toxins of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions normally would be administered as pharmaceutically acceptable compositions.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Anticipated administration is by intramuscular injection of 0.75 mg to 2 mg total doses of the combined multi-component toxins one to two times per month with gradual dose reduction as the subjects show decreased antigen-specific antibody titers. Moreover, for human administration, preparations should meet sterility, pyrogenicity, general safety and purity standards as required by FDA Office of Biologics standards.

All of the METHODS and COMPOSITIONS disclosed and claimed herein can be made and executed without undue experimentation in light of the present disclosure. It will be apparent to those of skill in the art that variations may be applied to the METHODS and COMPOSITIONS described herein without departing from the concept, spirit and scope of the claimed subject matter. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the claimed subject matter.

The invention claimed is:

1. A multi-component B-cell specific clonal toxin composition comprising:
    a first fusion molecule comprising a first targeting domain and an enzymatically active type I or type II ribosome inactivating polypeptide or active subunit thereof; and
    a second fusion molecule comprising a second targeting domain and a toxin translocation domain that is capable of interacting with and translocating the enzymatically active type I or type II ribosome inactivating polypeptide or active subunit thereof to the cytosol in a target B-cell, wherein the first fusion molecule is delivered to the cytosol only in the presence of the second fusion molecule, wherein the enzymatically active type I or type II ribosome inactivating polypeptide or active subunit thereof and the toxin translocation domain are not from the same native protein toxin and wherein the first and the second targeting domains bind to different receptors on the target B-cell.

2. The toxin according to claim 1, wherein the enzymatically active type I or type II ribosome inactivating polypeptide or active subunit thereof is selected from the group consisting of ricin, abrin, modeccin, viscumin, cholera, E. coli heat-labile, pertussis, Pseudomonas, shigella, and *diphtheria toxins*.

3. The toxin of claim 1, wherein the toxin translocation domain comprises a B chain of an A and B chain containing type II ribosome inactivating protein.

4. The toxin according to claim 3, wherein the toxin translocation domain comprises an Anthrax Protective Antigen or Clostridium Perfringens Iota toxin B chain.

5. The toxin according to claim 1, wherein one or both of the enzymatically active type I or type II ribosome inactivating polypeptide or active subunit thereof and the toxin translocation domain comprise one or more amino acid mutations as compared to a wild-type enzymatically active type I or type II ribosome inactivating polypeptide or active subunit thereof or toxin translocation domain.

6. The toxin according to claim 5, wherein one or more amino acid residues in the first toxin are substituted with other residues.

7. The toxin according to claim 6, wherein one or more wild-type residues in the enzymatically active type I or type II ribosome inactivating polypeptide or active subunit thereof are substituted with cysteine residues available for intermolecular disulfide bonding, wherein the toxin retains the ability to inactivate the target cell.

8. The toxin of claim 1, wherein the first targeting domain binds to an antibody displayed on the surface of a B-cell.

9. The toxin of claim 8, wherein the first targeting domain comprises an antigen.

10. The toxin of claim 9, wherein the antigen comprises a viral antigen.

11. The toxin of claim 10, wherein the viral antigen is selected from the group consisting of a capsid protein, a fiber protein, a penton protein, a hexon protein and a viral coat protein.

12. The toxin of claim 10, wherein the viral antigen comprises gp120.

13. The toxin of claim 8, wherein the first targeting domain comprises an anti-idiotypic antibody.

14. The toxin of claim 1, wherein the second targeting domain binds to a B-cell lineage specific marker.

15. The toxin of claim 14, wherein the second targeting domain comprises an antibody.

16. The toxin of claim 14, wherein the second targeting domain comprises an antigen-binding portion of an antibody, a Fab, a Fab', a F(ab')2, a Fv, a single variable domain, or a single-chain antibody fragment.

17. The toxin of claim 14, wherein the B-cell lineage specific marker is a lymphokine or cytokine specific to B-cells.

18. The multi-component B-cell specific clonal toxin composition of claim 1, wherein one or both of the toxin translocation domain and the enzymatically active type I or type II ribosome inactivating polypeptide or active subunit thereof comprise a toxin interaction region, and wherein the toxin interaction region must be processed within B-cells to permit interaction of the translocation domain and the enzymatically active type I or type II ribosome inactivating polypeptide or active subunit thereof.

19. The multi-component B-cell specific clonal toxin of claim 18, wherein the toxin interaction region comprises a poly-cationic tract.

20. The multi-component B-cell specific clonal toxin of claim 18, wherein the toxin interaction region comprises a poly-histidine tract.

* * * * *

SEQUENCE LISTING

<160> NUMBER OF SEQ ID NOS: 6

<210> SEQ ID NO 1
<211> LENGTH: 506
<212> TYPE: PRT
<213> ORGANISM: Indian (clade C) consensus human immunodeficiency virus

<400> SEQUENCE: 1

```
Met Lys Val Lys Glu Thr Arg Arg Asn Tyr Gln His Leu Trp Arg Trp
1               5                   10                  15

Gly Ile Met Leu Leu Gly Ile Leu Met Ile Cys Ser Ala Thr Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60
```

-continued

```
His Asn Val Trp Ala Thr His Ala Cys Val Pro Thr Asp Pro Asn Pro
 65                  70                  75                  80

Gln Glu Val Val Leu Gly Asn Val Thr Glu Asn Phe Asn Met Trp Lys
                 85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Val Thr Leu Asn Cys Thr
        115                 120                 125

Asp Leu Gly Lys Ala Thr Asn Thr Thr Ser Ser Asn Trp Glu Lys Met
    130                 135                 140

Glu Lys Gly Glu Ile Lys Asn Cys Ser Phe Asn Ile Thr Thr Ser Ile
145                 150                 155                 160

Arg Asp Lys Val Gln Lys Glu Tyr Ala Leu Phe Tyr Lys Leu Asp Ile
                165                 170                 175

Val Pro Ile Asp Asn Asn Ser Asn Thr Thr Asn Asn Thr Ser Tyr Arg
            180                 185                 190

Leu Ile Ser Cys Asn Thr Ser Val Ile Thr Gln Ala Cys Pro Lys Val
        195                 200                 205

Ser Phe Glu Pro Ile Pro Ile His Tyr Cys Thr Pro Ala Gly Phe Ala
    210                 215                 220

Ile Leu Lys Cys Asn Asp Lys Lys Phe Asn Gly Lys Gly Pro Cys Lys
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Glu Asn Phe Thr Asn Asn Ala Lys Thr Ile Ile Val Gln Leu
        275                 280                 285

Lys Glu Ser Val Glu Ile Asn Cys Thr Arg Pro Asn Asn Asn Thr Arg
    290                 295                 300

Lys Ser Ile His Ile Gly Pro Gly Ala Ala Phe Tyr Thr Thr Gly Glu
305                 310                 315                 320

Ile Ile Gly Asp Ile Arg Gln Ala His Cys Asn Ile Ser Arg Ala Lys
                325                 330                 335

Trp Asn Asn Thr Leu Lys Gln Ile Val Lys Lys Leu Arg Glu Gln Phe
            340                 345                 350

Gly Asn Lys Ile Val Phe Asn Gln Ser Ser Gly Gly Lys Pro Arg Ile
        355                 360                 365

Val Thr His Ser Phe Asn Cys Gly Gly Glu Phe Phe Tyr Cys Asn Thr
    370                 375                 380

Thr Gln Leu Phe Asn Ser Thr Thr Arg Ser Thr Asn Asn Thr Glu
385                 390                 395                 400

Gly Ser Asn Asn Thr Asp Thr Ile Thr Thr Leu Pro Cys Arg Ala Asp
                405                 410                 415

Ala Ile Ile Asn Arg Trp Gln Glu Val Gly Lys Ala Met Tyr Ala Pro
            420                 425                 430

Pro Ile Arg Gly Gln Ile Arg Cys Ser Ser Asn Ile Thr Gly Leu Leu
        435                 440                 445

Leu Thr Arg Asp Gly Gly Thr Asn Thr Asn Asp Thr Glu Ile Phe Arg
    450                 455                 460

Pro Gly Gly Gly Asp Met Arg Asp Asn Trp Arg Ser Glu Leu Tyr Lys
465                 470                 475                 480
```

```
Tyr Lys Val Val Lys Ile Glu Pro Leu Gly Val Ala Pro Thr Lys Ala
            485                 490                 495

Lys Arg Arg Val Val Gln Arg Glu Lys Arg
            500                 505

<210> SEQ ID NO 2
<211> LENGTH: 129
<212> TYPE: PRT
<213> ORGANISM: Human IL-4

<400> SEQUENCE: 2

His Lys Cys Asp Ile Thr Leu Gln Glu Ile Ile Lys Thr Leu Asn Ser
1               5                   10                  15

Leu Thr Glu Asn Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Asp Ser Lys Cys Ser
            115                 120                 125

Ser

<210> SEQ ID NO 3
<211> LENGTH: 735
<212> TYPE: PRT
<213> ORGANISM: Anthrax

<400> SEQUENCE: 3

Glu Val Lys Gln Glu Asn Arg Leu Leu Asn Glu Ser Glu Ser Ser Ser
1               5                   10                  15

Gln Gly Leu Leu Gly Tyr Tyr Phe Ser Asp Leu Asn Phe Gln Ala Pro
            20                  25                  30

Met Val Val Thr Ser Ser Thr Thr Gly Asp Leu Ser Ile Pro Ser Ser
            35                  40                  45

Glu Leu Glu Asn Ile Pro Ser Glu Asn Gln Tyr Phe Gln Ser Ala Ile
    50                  55                  60

Trp Ser Gly Phe Ile Lys Val Lys Lys Ser Asp Glu Tyr Thr Phe Ala
65                  70                  75                  80

Thr Ser Ala Asp Asn His Val Thr Met Trp Val Asp Asp Gln Glu Val
                85                  90                  95

Ile Asn Lys Ala Ser Asn Ser Asn Lys Ile Arg Leu Glu Lys Gly Arg
            100                 105                 110

Leu Tyr Gln Ile Lys Ile Gln Tyr Gln Arg Glu Asn Pro Thr Glu Lys
            115                 120                 125

Gly Leu Asp Phe Lys Leu Tyr Trp Thr Asp Ser Gln Asn Lys Lys Glu
            130                 135                 140

Val Ile Ser Ser Asp Asn Leu Gln Leu Pro Glu Leu Lys Gln Lys Ser
145                 150                 155                 160

Ser Asn Ser Arg Lys Lys Arg Ser Thr Ser Ala Gly Pro Thr Val Pro
```

```
                165                 170                 175
Asp Arg Asp Asn Asp Gly Ile Pro Asp Ser Leu Glu Val Glu Gly Tyr
            180                 185                 190
Thr Val Asp Val Lys Asn Lys Arg Thr Phe Leu Ser Pro Trp Ile Ser
            195                 200                 205
Asn Ile His Glu Lys Lys Gly Leu Thr Lys Tyr Lys Ser Ser Pro Glu
            210                 215                 220
Lys Trp Ser Thr Ala Ser Asp Pro Tyr Ser Asp Phe Glu Lys Val Thr
225                 230                 235                 240
Gly Arg Ile Asp Lys Asn Val Ser Pro Glu Ala Arg His Pro Leu Val
            245                 250                 255
Ala Ala Tyr Pro Ile Val His Val Asp Met Glu Asn Ile Ile Leu Ser
            260                 265                 270
Lys Asn Glu Asp Gln Ser Thr Gln Asn Thr Asp Ser Glu Thr Arg Thr
            275                 280                 285
Ile Ser Lys Asn Thr Ser Thr Ser Arg Thr His Thr Ser Glu Val His
            290                 295                 300
Gly Asn Ala Glu Val His Ala Ser Phe Phe Asp Ile Gly Gly Ser Val
305                 310                 315                 320
Ser Ala Gly Phe Ser Asn Ser Asn Ser Ser Thr Val Ala Ile Asp His
            325                 330                 335
Ser Leu Ser Leu Ala Gly Glu Arg Thr Trp Ala Glu Thr Met Gly Leu
            340                 345                 350
Asn Thr Ala Asp Thr Ala Arg Leu Asn Ala Asn Ile Arg Tyr Val Asn
            355                 360                 365
Thr Gly Thr Ala Pro Ile Tyr Asn Val Leu Pro Thr Thr Ser Leu Val
            370                 375                 380
Leu Gly Lys Asn Gln Thr Leu Ala Thr Ile Lys Ala Lys Glu Asn Gln
385                 390                 395                 400
Leu Ser Gln Ile Leu Ala Pro Asn Asn Tyr Tyr Pro Ser Lys Asn Leu
            405                 410                 415
Ala Pro Ile Ala Leu Asn Ala Gln Asp Asp Phe Ser Ser Thr Pro Ile
            420                 425                 430
Thr Met Asn Tyr Asn Gln Phe Leu Glu Leu Glu Lys Thr Lys Gln Leu
            435                 440                 445
Arg Leu Asp Thr Asp Gln Val Tyr Gly Asn Ile Ala Thr Tyr Asn Phe
            450                 455                 460
Glu Asn Gly Arg Val Arg Val Asp Thr Gly Ser Asn Trp Ser Glu Val
465                 470                 475                 480
Leu Pro Gln Ile Gln Glu Thr Thr Ala Arg Ile Ile Phe Asn Gly Lys
            485                 490                 495
Asp Leu Asn Leu Val Glu Arg Arg Ile Ala Ala Val Asn Pro Ser Asp
            500                 505                 510
Pro Leu Glu Thr Thr Lys Pro Asp Met Thr Leu Lys Glu Ala Leu Lys
            515                 520                 525
Ile Ala Phe Gly Phe Asn Glu Pro Asn Gly Asn Leu Gln Tyr Gln Gly
            530                 535                 540
Lys Asp Ile Thr Glu Phe Asp Phe Asn Phe Asp Gln Gln Thr Ser Gln
545                 550                 555                 560
Asn Ile Lys Asn Gln Leu Ala Glu Leu Asn Ala Thr Asn Ile Tyr Thr
            565                 570                 575
Val Leu Asp Lys Ile Lys Leu Asn Ala Lys Met Asn Ile Leu Ile Arg
            580                 585                 590
```

```
Asp Lys Arg Phe His Tyr Asp Arg Asn Asn Ile Ala Val Gly Ala Asp
            595                 600                 605

Glu Ser Val Val Lys Glu Ala His Arg Glu Val Ile Asn Ser Ser Thr
            610                 615                 620

Glu Gly Leu Leu Leu Asn Ile Asp Lys Asp Ile Arg Lys Ile Leu Ser
625                 630                 635                 640

Gly Tyr Ile Val Glu Ile Glu Asp Thr Glu Gly Leu Lys Glu Val Ile
            645                 650                 655

Asn Asp Arg Tyr Asp Met Leu Asn Ile Ser Ser Leu Arg Gln Asp Gly
            660                 665                 670

Lys Thr Phe Ile Asp Phe Lys Lys Tyr Asn Asp Lys Leu Pro Leu Tyr
            675                 680                 685

Ile Ser Asn Pro Asn Tyr Lys Val Asn Val Tyr Ala Val Thr Lys Glu
            690                 695                 700

Asn Thr Ile Ile Asn Pro Ser Glu Asn Gly Asp Thr Ser Thr Asn Gly
705                 710                 715                 720

Ile Lys Lys Ile Leu Ile Phe Ser Lys Lys Gly Tyr Glu Ile Gly
            725                 730                 735

<210> SEQ ID NO 4
<211> LENGTH: 193
<212> TYPE: PRT
<213> ORGANISM: Diphtheria

<400> SEQUENCE: 4

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
            35                  40                  45

Asp Trp Lys Gly Phe Tyr Ser Thr Asp Asn Lys Tyr Asp Ala Ala Gly
        50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
            115                 120                 125

Asp Gly Ala Ser Arg Val Val Leu Ser Leu Pro Phe Ala Glu Gly Ser
        130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg

<210> SEQ ID NO 5
<211> LENGTH: 725
<212> TYPE: PRT
<213> ORGANISM: Artificial Sequence
```

```
<220> FEATURE:
<223> OTHER INFORMATION: an acid-dependant polycationic octahistidine
      tract, followed by a linker segment, followed by sequence from
      truncated Diphtheria, followed by a proteolytically cleavable
      linker, followed by a modified consensus C clade HIV gp120

<400> SEQUENCE: 5
```

| | | | | | | | | | | | | | | |
|---|---|---|---|---|---|---|---|---|---|---|---|---|---|---|
|His|His|His|His|His|His|His|His|Ser|Ser|Gly|Ser|Ser|Gly|Gly|Ala|
|1| | |5| | | | |10| | | |15| | |

Asp Asp Val Val Asp Ser Ser Lys Ser Phe Val Met Glu Asn Phe Ser
            20                  25                  30

Ser Tyr His Gly Thr Lys Pro Gly Tyr Val Asp Ser Ile Gln Lys Gly
        35                  40                  45

Ile Gln Lys Pro Lys Ser Gly Thr Gln Gly Asn Tyr Asp Asp Asp Trp
50                  55                  60

Lys Gly Phe Tyr Ser Thr Asp Asn Lys Tyr Asp Ala Ala Gly Tyr Ser
65                  70                  75                  80

Val Asp Asn Glu Asn Pro Leu Ser Gly Lys Ala Gly Gly Val Val Lys
                85                  90                  95

Val Thr Tyr Pro Gly Leu Thr Lys Val Leu Ala Leu Lys Val Asp Asn
                100                 105                 110

Ala Glu Thr Ile Lys Lys Glu Leu Gly Leu Ser Leu Thr Glu Pro Leu
            115                 120                 125

Met Glu Gln Val Gly Thr Glu Glu Phe Ile Lys Arg Phe Gly Asp Gly
        130                 135                 140

Ala Ser Arg Val Val Leu Ser Leu Pro Phe Ala Glu Gly Ser Ser Ser
145                 150                 155                 160

Val Glu Tyr Ile Asn Asn Trp Glu Gln Ala Lys Ala Leu Ser Val Glu
                165                 170                 175

Leu Glu Ile Asn Phe Glu Thr Arg Gly Lys Arg Gly Gln Asp Ala Met
                180                 185                 190

Tyr Glu Tyr Met Ala Gln Ala Ser Ala Gly Asn Arg Val Arg Arg Ser
            195                 200                 205

Ser Gly Arg Val Arg Arg Ser Ser Gly Ser Ser Gly Met Arg Val Arg
210                 215                 220

Gly Thr Leu Arg Asn Tyr Gln Gln Trp Glu Ile Trp Gly Ile Leu Gly
225                 230                 235                 240

Phe Trp Met Leu Met Ile Cys Asn Val Gly Asn Leu Trp Val Thr
                245                 250                 255

Val Tyr Tyr Gly Val Pro Val Trp Lys Glu Ala Lys Thr Thr Leu Phe
            260                 265                 270

Cys Ala Ser Asp Ala Lys Ala Tyr Glu Lys Glu Val His Asn Val Trp
            275                 280                 285

Ala Thr His Ala Cys Val Pro Thr Asp Pro Asn Pro Gln Glu Ile Val
            290                 295                 300

Leu Glu Asn Val Thr Glu Asn Phe Asn Met Trp Lys Asn Asp Met Val
305                 310                 315                 320

Asn Gln Met His Glu Asp Val Ile Ser Leu Trp Asp Gln Ser Leu Lys
                325                 330                 335

Pro Cys Val Lys Leu Thr Pro Leu Cys Val Thr Leu Glu Cys Arg Asn
                340                 345                 350

Val Thr Ser Asn Gly Thr Thr Tyr Thr Glu Ser Val Glu Glu Ile Lys
            355                 360                 365

Asn Cys Ser Phe Asn Thr Thr Thr Glu Ile Arg Asp Arg Lys Gln Lys
            370                 375                 380

```
Val Tyr Ala Leu Phe Tyr Arg Leu Asp Ile Val Pro Leu Asn Glu Asn
385                 390                 395                 400

Asn Ser Asn Ser Ser Asn Ser Glu Tyr Tyr Arg Leu Ile Asn Cys
        405                 410                 415

Asn Thr Ser Ala Ile Thr Gln Ala Cys Pro Lys Val Thr Phe Asp Pro
            420                 425                 430

Ile Pro Ile His Tyr Cys Ala Pro Ala Gly Tyr Ala Ile Leu Lys Cys
            435                 440                 445

Asn Asp Lys Thr Phe Asn Gly Thr Gly Pro Cys His Asn Val Ser Thr
450                 455                 460

Val Gln Cys Thr His Gly Ile Lys Pro Val Val Ser Thr Gln Leu Leu
465                 470                 475                 480

Leu Asn Gly Ser Leu Ala Glu Gly Glu Ile Ile Arg Ser Glu Asn
                485                 490                 495

Leu Thr Asn Asn Val Lys Thr Ile Ile Val His Leu Asn Gln Ser Val
            500                 505                 510

Glu Ile Val Cys Thr Arg Pro Asn Asn Asn Thr Arg Lys Ser Ile Arg
515                 520                 525

Ile Gly Pro Gly Gln Thr Phe Tyr Ala Thr Gly Glu Ile Ile Gly Asp
530                 535                 540

Ile Arg Gln Ala His Cys Asn Ile Ser Glu Asp Lys Trp Asn Glu Thr
545                 550                 555                 560

Leu Gln Arg Val Gly Lys Lys Leu Ala Glu His Phe Pro Asn Lys Thr
                565                 570                 575

Ile Lys Phe Ala Ser Ser Ser Gly Gly Lys Pro Arg Ile Thr Thr His
            580                 585                 590

Ser Phe Asn Cys Arg Gly Glu Phe Phe Tyr Cys Asn Thr Ser Gly Leu
            595                 600                 605

Phe Asn Gly Thr Thr Thr Arg Thr Asp Thr Lys Asn Ser Ser Asn Ser
            610                 615                 620

Asn Thr Ile Thr Ile Pro Cys Arg Ala Asp Ala Ile Ile Asn Met Trp
625                 630                 635                 640

Gln Glu Val Gly Arg Ala Met Tyr Ala Pro Pro Ile Glu Gly Asn Ile
                645                 650                 655

Thr Cys Lys Ser Asn Ile Thr Gly Leu Leu Leu Val Arg Asp Gly Gly
            660                 665                 670

Thr Glu Glu Thr Asn Lys Thr Glu Thr Phe Arg Pro Gly Gly Gly Asp
            675                 680                 685

Met Arg Asp Asn Trp Arg Ser Glu Leu Tyr Lys Tyr Lys Val Val Glu
690                 695                 700

Ile Lys Pro Leu Gly Val Ala Pro Thr Glu Ala Lys Arg Arg Val Val
705                 710                 715                 720

Glu Arg Glu Lys Arg
                725

<210> SEQ ID NO 6
<211> LENGTH: 709
<212> TYPE: PRT
<213> ORGANISM: Artificial Sequence
<220> FEATURE:
<223> OTHER INFORMATION: truncated Anthrax PA, followed by a linker,
      followed by a sequence from hIL-4 antagonist

<400> SEQUENCE: 6

Leu Leu Gly Tyr Tyr Phe Ser Asp Leu Asn Phe Gln Ala Pro Met Val
```

-continued

```
1               5                   10                  15
Val Thr Ser Ser Thr Thr Gly Asp Leu Ser Ile Pro Ser Glu Leu Glu
                20                  25                  30
Asn Ile Pro Ser Glu Asn Gln Tyr Phe Gln Ser Ala Ile Trp Ser Gly
            35                  40                  45
Phe Ile Lys Val Lys Lys Ser Asp Glu Tyr Thr Phe Ala Thr Ser Ala
        50                  55                  60
Asp Asn His Val Thr Met Trp Val Asp Gln Glu Val Ile Asn Lys
65                  70                  75                  80
Ala Ser Asn Ser Asn Lys Ile Arg Leu Glu Lys Gly Arg Leu Tyr Gln
                85                  90                  95
Ile Lys Ile Gln Tyr Gln Arg Glu Asn Pro Thr Glu Lys Gly Leu Asp
            100                 105                 110
Phe Lys Leu Tyr Trp Thr Asp Ser Gln Asn Lys Lys Glu Val Ile Ser
        115                 120                 125
Ser Asp Asn Leu Gln Leu Pro Glu Leu Lys Gln Lys Ser Ser Asn Ser
        130                 135                 140
Arg Val Arg Arg Ser Thr Ser Ala Gly Pro Thr Val Pro Asp Arg Asp
145                 150                 155                 160
Asn Asp Gly Ile Pro Asp Ser Leu Glu Val Glu Gly Tyr Thr Val Asp
                165                 170                 175
Val Lys Asn Lys Arg Thr Phe Leu Ser Pro Trp Ile Ser Asn Ile His
            180                 185                 190
Glu Lys Lys Gly Leu Thr Lys Tyr Lys Ser Ser Pro Glu Lys Trp Ser
        195                 200                 205
Thr Ala Ser Asp Pro Tyr Ser Asp Phe Glu Lys Val Thr Gly Arg Ile
    210                 215                 220
Asp Lys Asn Val Ser Pro Glu Ala Arg His Pro Leu Val Ala Ala Tyr
225                 230                 235                 240
Pro Ile Val His Val Asp Met Glu Asn Ile Ile Leu Ser Lys Asn Glu
                245                 250                 255
Asp Gln Ser Thr Gln Asn Thr Asp Ser Glu Thr Arg Thr Ile Ser Lys
            260                 265                 270
Asn Thr Ser Thr Ser Arg Thr His Thr Ser Glu Val His Gly Asn Ala
        275                 280                 285
Glu Val His Ala Ser Phe Phe Asp Ile Gly Ser Val Ser Ala Gly Phe
    290                 295                 300
Ser Asn Ser Asn Ser Ser Thr Val Ala Ile Asp His Ser Leu Ser Leu
305                 310                 315                 320
Ala Gly Glu Arg Thr Trp Ala Glu Thr Met Gly Leu Asn Thr Ala Asp
                325                 330                 335
Thr Ala Arg Leu Asn Ala Asn Ile Arg Tyr Val Asn Thr Gly Thr Ala
            340                 345                 350
Pro Ile Tyr Asn Val Leu Pro Thr Thr Ser Leu Val Leu Gly Lys Asn
        355                 360                 365
Gln Thr Leu Ala Thr Ile Lys Ala Lys Glu Asn Gln Leu Ser Gln Ile
    370                 375                 380
Leu Ala Pro Asn Asn Tyr Tyr Pro Ser Lys Asn Leu Ala Pro Ile Ala
385                 390                 395                 400
Leu Asn Ala Gln Asp Asp Phe Ser Ser Thr Pro Ile Thr Met Asn Tyr
                405                 410                 415
Asn Gln Phe Leu Glu Leu Glu Lys Thr Lys Gln Leu Arg Leu Asp Thr
            420                 425                 430
```

-continued

```
Asp Gln Val Tyr Gly Asn Ile Ala Thr Tyr Asn Phe Glu Asn Gly Arg
        435                 440                 445

Val Arg Val Asp Thr Gly Ser Asn Trp Ser Glu Val Leu Pro Gln Ile
        450                 455                 460

Gln Glu Thr Thr Ala Arg Ile Ile Phe Asn Gly Lys Asp Leu Asn Leu
465                 470                 475                 480

Val Glu Arg Arg Ile Ala Ala Val Asn Pro Ser Asp Pro Leu Glu Thr
                485                 490                 495

Thr Lys Pro Asp Met Thr Leu Lys Glu Ala Leu Lys Ile Ala Phe Gly
            500                 505                 510

Phe Asn Glu Pro Asn Gly Asn Leu Gln Tyr Gln Gly Lys Asp Ile Thr
            515                 520                 525

Glu Phe Asp Phe Asn Phe Asp Gln Gln Thr Ser Gln Asn Ile Lys Asn
            530                 535                 540

Gln Leu Ala Glu Leu Asn Ala Thr Asn Ile Tyr Thr Val Leu Asp Ile
545                 550                 555                 560

Lys Leu Asn Ala Lys Met Asn Ile Leu Ile Arg Asp Lys Arg Ser Ser
                565                 570                 575

Gly Ser Ser Gly His Lys Cys Asp Ile Thr Leu Gln Glu Ile Ile Lys
            580                 585                 590

Thr Leu Asn Ser Leu Thr Glu Asn Lys Thr Leu Cys Thr Glu Leu Thr
            595                 600                 605

Val Thr Asp Ile Phe Ala Ala Ser Lys Asn Thr Thr Glu Lys Glu Thr
        610                 615                 620

Phe Cys Arg Ala Ala Thr Val Leu Arg Gln Phe Tyr Ser His His Glu
625                 630                 635                 640

Lys Asp Thr Arg Cys Leu Gly Ala Thr Ala Gln Gln Phe His His Arg His
                645                 650                 655

Lys Gln Leu Ile Arg Phe Leu Lys Arg Leu Asp Arg Asn Leu Trp Gly
                660                 665                 670

Leu Ala Gly Leu Asn Ser Cys Pro Val Lys Glu Ala Asn Gln Ser Thr
            675                 680                 685

Leu Glu Asn Phe Leu Glu Arg Leu Lys Thr Ile Met Arg Glu Lys Asp
            690                 695                 700

Ser Lys Cys Ser Ser
705
```